United States Patent
Augustine et al.

(10) Patent No.: US 7,543,344 B2
(45) Date of Patent: Jun. 9, 2009

(54) COVER FOR A HEATING BLANKET

(75) Inventors: Scott D. Augustine, Bloomington, MN (US); Randall C. Arnold, Minnetonka, MN (US); Rudolf A. Deibel, Eden Prairie, MN (US); Scott A. Entenman, St. Paul, MN (US); Keith J. Leland, Medina, MN (US); Thomas F. Neils, Minneapolis, MN (US)

(73) Assignee: Augustine Biomedical and Design LLC, Eden Prairie, MN (US)

( * ) Notice: Subject to any disclaimer, the term of this patent is extended or adjusted under 35 U.S.C. 154(b) by 140 days.

(21) Appl. No.: 11/537,114

(22) Filed: Sep. 29, 2006

(65) Prior Publication Data
US 2007/0067910 A1 Mar. 29, 2007

Related U.S. Application Data

(60) Provisional application No. 60/722,242, filed on Sep. 29, 2005, provisional application No. 60/722,243, filed on Sep. 29, 2005.

(51) Int. Cl.
A47G 9/02 (2006.01)
(52) U.S. Cl. .................... 5/423; 5/501; 5/502; 5/485
(58) Field of Classification Search .............. 5/423, 5/484, 485, 487, 494, 496, 498, 501, 502, 5/941
See application file for complete search history.

(56) References Cited

U.S. PATENT DOCUMENTS

| | | | | |
|---|---|---|---|---|
| 2,497,186 A | * | 2/1950 | Pedersen | 5/498 |
| 3,008,152 A | * | 11/1961 | Seidenberg | 5/501 |
| 3,137,871 A | * | 6/1964 | Florio | 5/487 |
| 3,340,549 A | * | 9/1967 | Billerbeck | 5/502 |
| 3,808,403 A | | 4/1974 | Kanaya et al. | |
| 4,149,066 A | | 4/1979 | Niibe | |
| 4,534,886 A | | 8/1985 | Kraus et al. | |
| 4,626,664 A | | 12/1986 | Grise | |
| 4,660,388 A | * | 4/1987 | Greene, Jr. | 62/261 |
| 4,764,665 A | | 8/1988 | Orban et al. | |
| 4,912,306 A | | 3/1990 | Grise et al. | |
| 5,023,433 A | | 6/1991 | Gordon | |
| 5,473,783 A | * | 12/1995 | Allen | 5/652.2 |
| 5,817,145 A | | 10/1998 | Augustine et al. | |
| 5,824,996 A | | 10/1998 | Kochman et al. | |
| 5,986,243 A | | 11/1999 | Campf | |
| 6,078,026 A | | 6/2000 | West | |
| 6,172,344 B1 | | 1/2001 | Gordon et al. | |
| 6,483,087 B2 | | 11/2002 | Gardner et al. | |
| 6,493,889 B2 | * | 12/2002 | Kocurek | 5/423 |
| 6,770,848 B2 | | 8/2004 | Haas et al. | |
| 6,770,854 B1 | | 8/2004 | Keane | |
| 6,974,935 B2 | | 12/2005 | O'Grady | |
| 7,013,509 B2 | * | 3/2006 | Hickman | 5/485 |
| 7,022,950 B2 | | 4/2006 | Haas et al. | |
| 7,181,790 B2 | * | 2/2007 | Wirtz | 5/501 |
| 7,228,578 B2 | * | 6/2007 | Linnane | 5/485 |

\* cited by examiner

*Primary Examiner*—Michael Trettel
(74) *Attorney, Agent, or Firm*—Fredrikson & Byron, P.A.

(57) ABSTRACT

A cover includes an enclosure for a heating blanket which is formed between an upper sheet bonded to a lower sheet of the cover. An opening for the enclosure is formed by a panel of the upper sheet which is separable from the lower sheet.

50 Claims, 7 Drawing Sheets

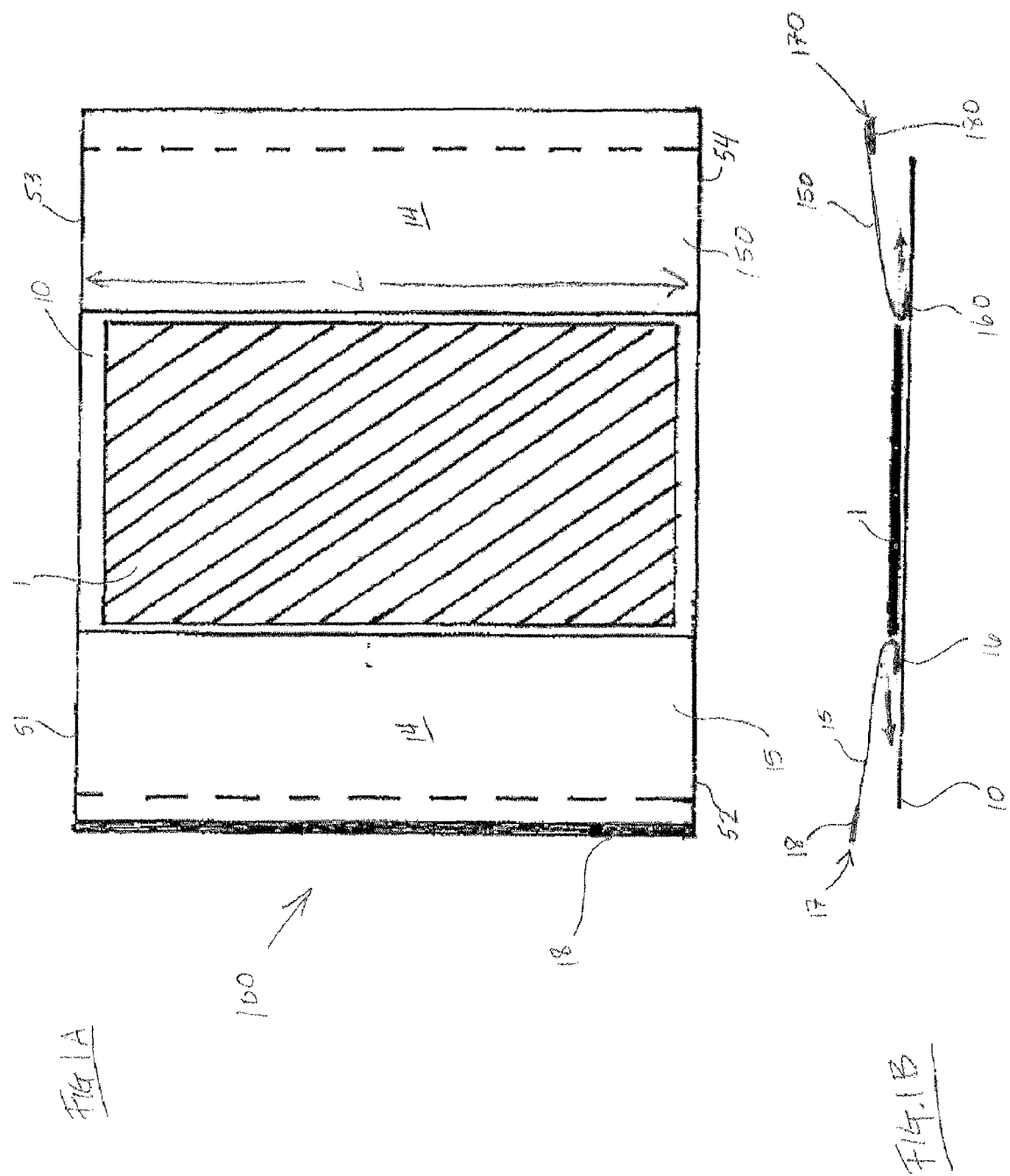

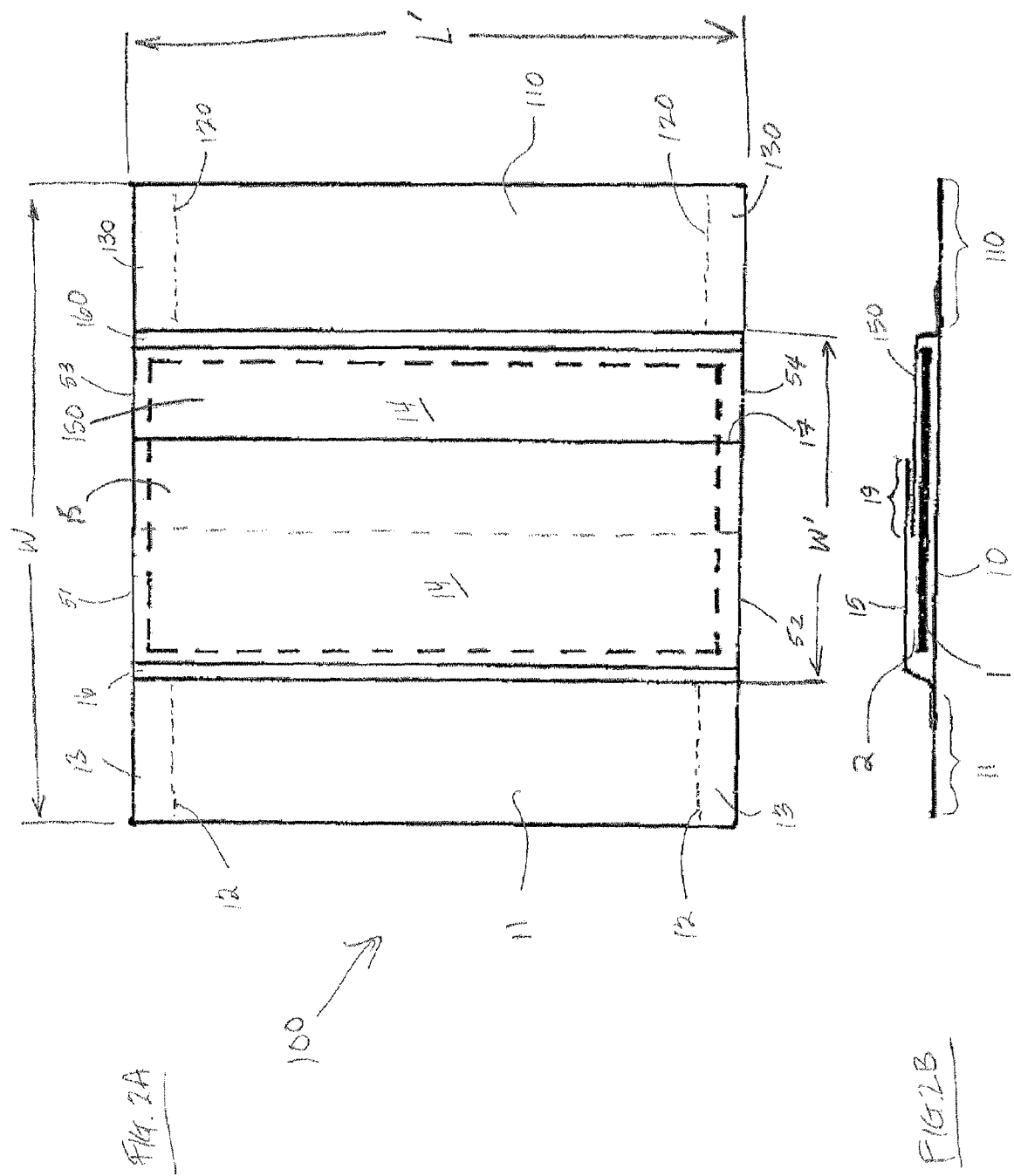

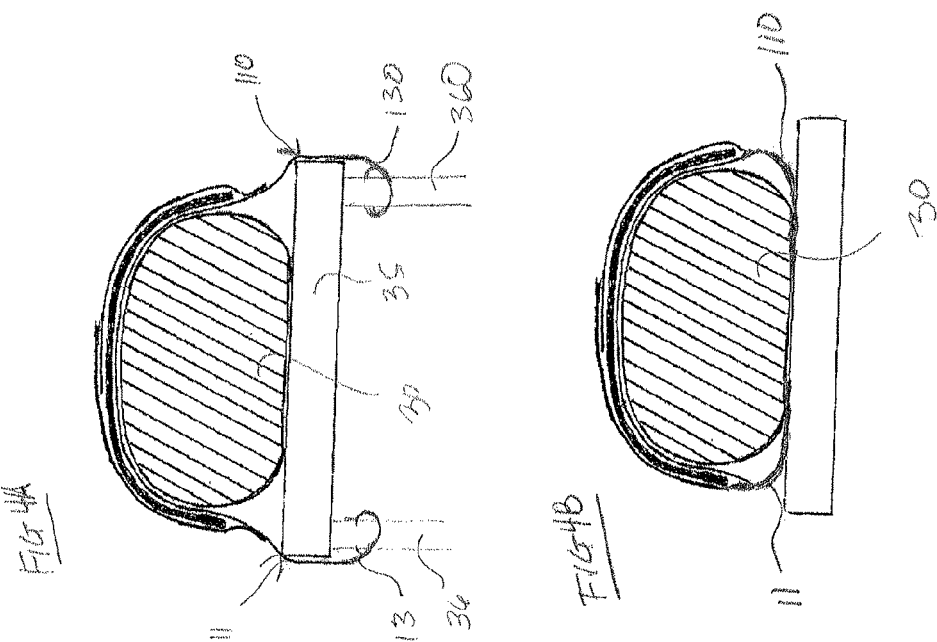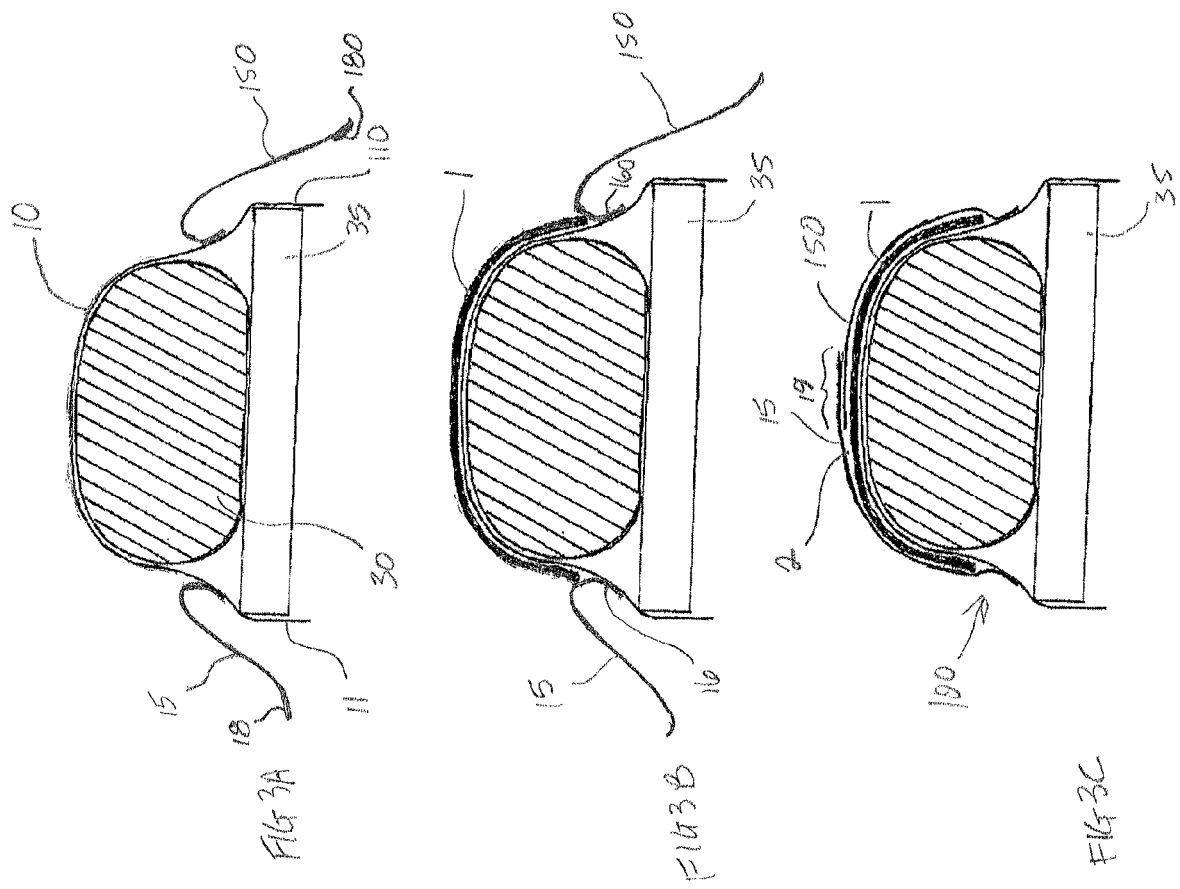

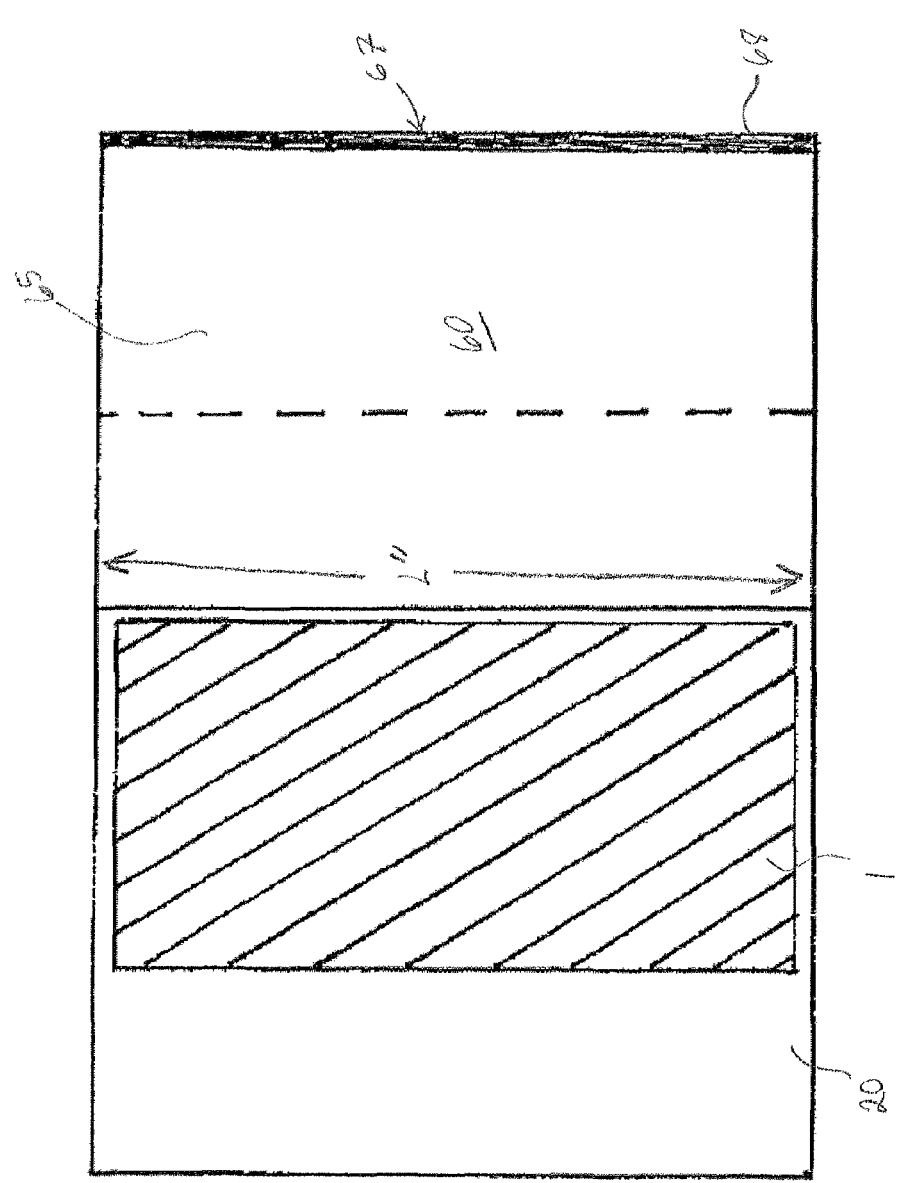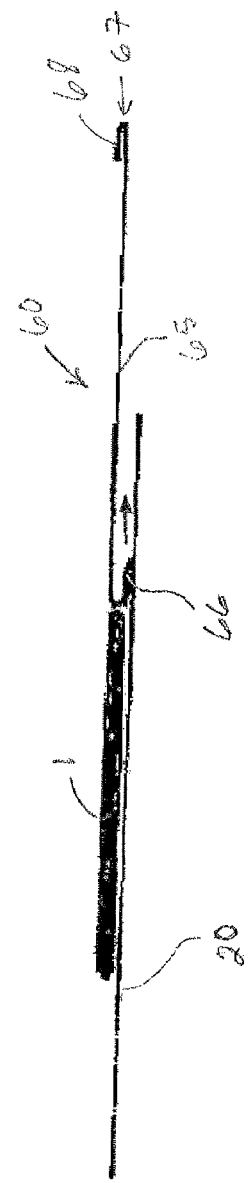

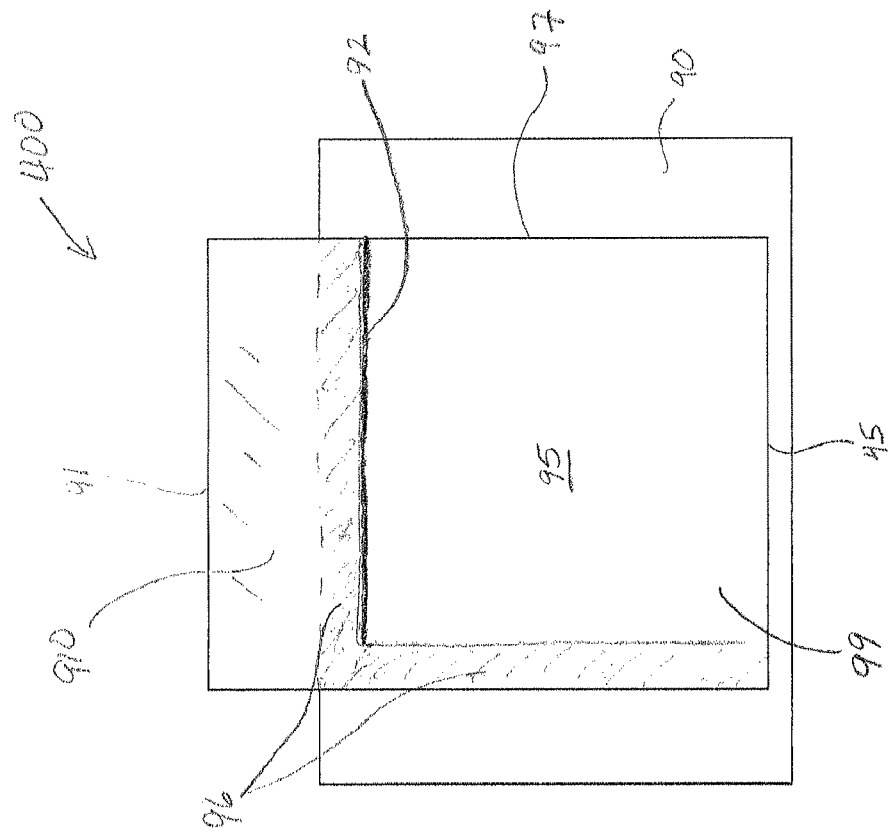
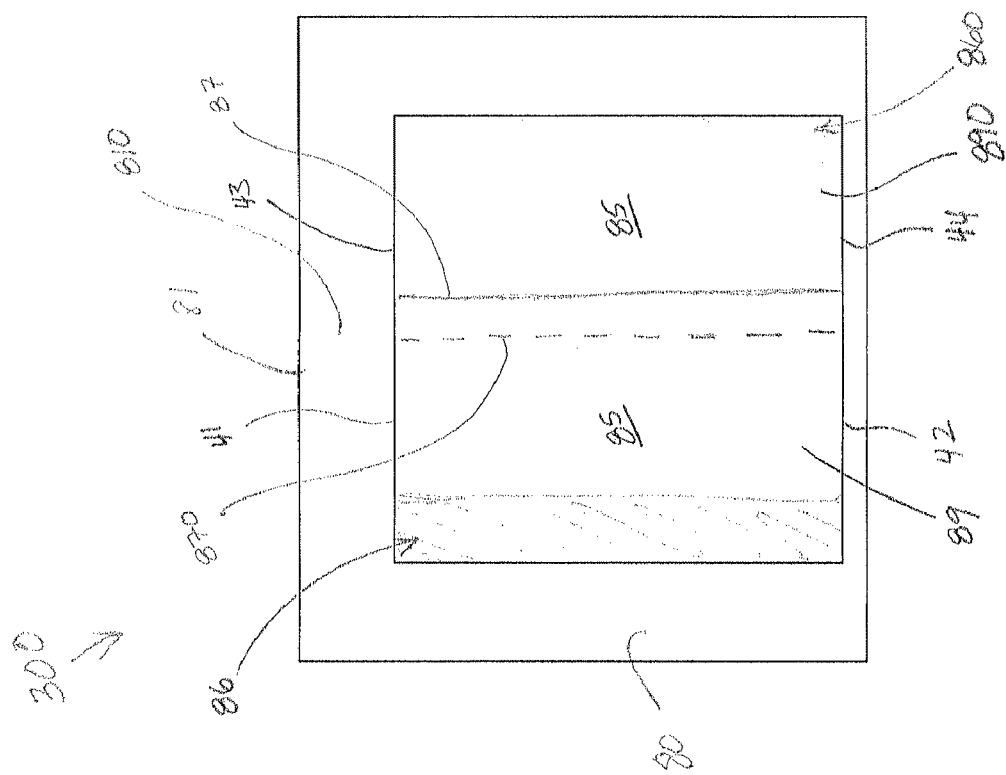

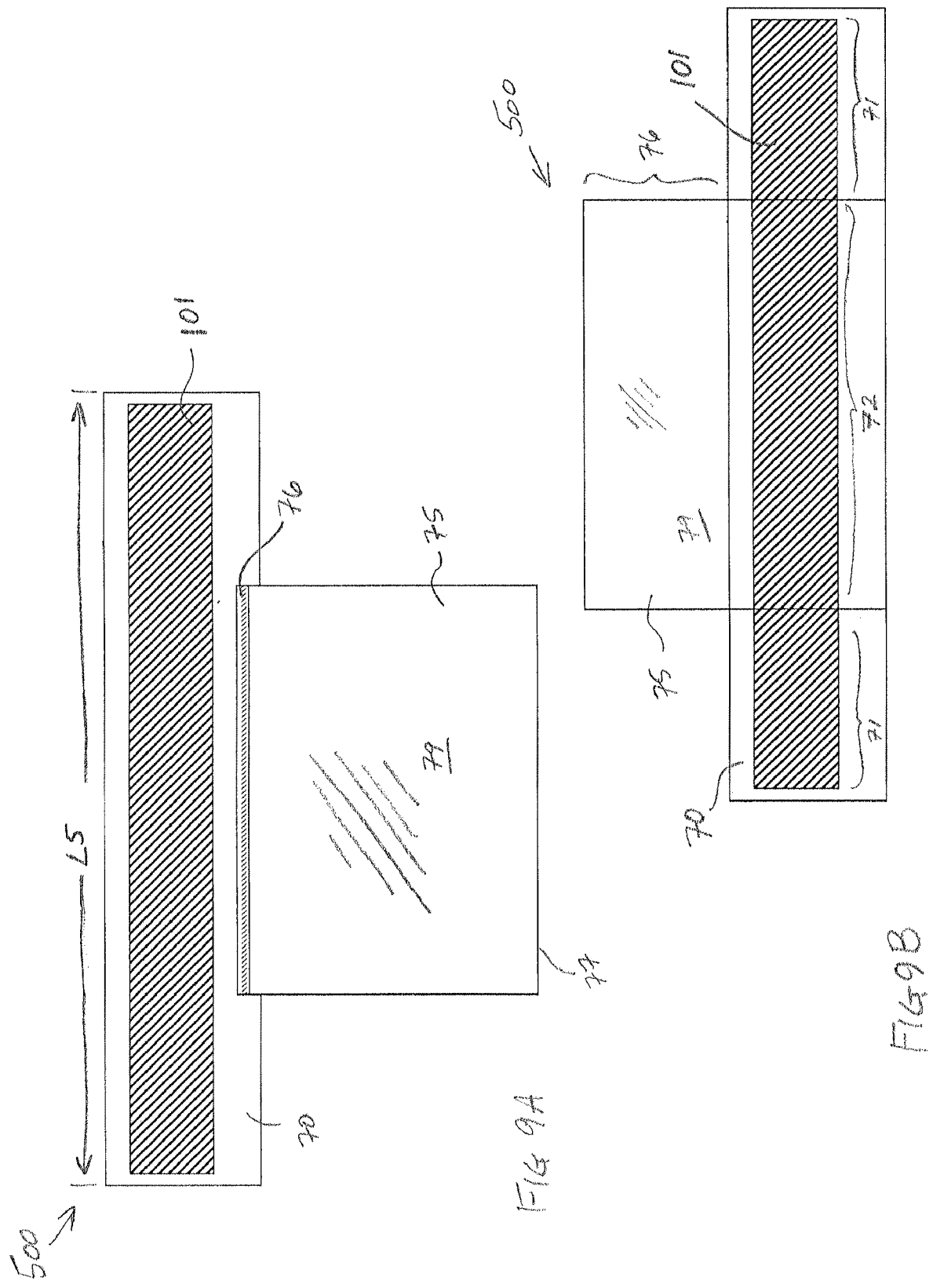

COVER FOR A HEATING BLANKET

PRIORITY CLAIM AND RELATED APPLICATION

The present application claims priority to provisional application Ser. No. 60/722,242 filed Sep. 29, 2005 having the same title, and to provisional application Ser. No. 60/722,243 filed Sep. 29, 2005 entitled HEATING BLANKET COVER CONSTRUCTION AND METHODS OF MANUFACTURE, both of which are hereby incorporated in their entireties. The present application is related to the commonly assigned application entitled, HEATING BLANKET COVER CONSTRUCTION AND METHODS OF MANUFACTURE, concurrently filed herewith and incorporated by reference in its entirety herein.

TECHNICAL FIELD

The present invention pertains to flexible covers and more particularly to covers for heating units, for example, electric blankets or pads, which may be used to keep patients warm during medical procedures.

BACKGROUND

For over a decade, forced-air warming (FAW), via an inflatable air blanket, has been used in operating rooms to prevent hypothermia in surgical patients. It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic, if not warmed. FAW has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket. Although FAW is clinically effective, it suffers from several problems including: a relatively high price; air blowing in the operating room, which can be noisy and can potentially contaminate the surgical field; and the inflatable blanket is relatively bulky over the patient, at times even obscuring the view of the surgeon. Moreover, the low specific heat of air and the rapid loss of heat from air requires that the temperature of the air, as it leaves the hose, be dangerously high—in some products as high as 45° C. This creates significant dangers for the patient. Second and third degree burns have occurred both because of contact between the hose and the patient's skin, and by blowing hot air directly from the hose onto the skin, without connecting a blanket to the hose. This condition is common enough to have its own name—"hosing." The manufacturers of forced air warming equipment actively warn their users against hosing and the risks it poses to the patient.

The logistics of FAW and the bulk of the inflatable air blankets have motivated the development of electric or warm water circulating heating blankets. Many of these heating blankets are reusable so that the blankets must either be cleaned between uses, or the blankets must be enclosed in a clean cover for each use. Inadequate cleaning can cause cross contamination between patients. Cleaning is not only time consuming during the rapid turnover of the operating room after each case, but the labor for the cleaning is also expensive. Some reusable covers are formed with pockets having an open edge. This edge access point is ideal for inserting small, stiff heater cards or pads into small pockets. However, if the heater is flexible and is large, the size of a blanket, inserting it into a protective pocket from the side, is nearly impossible. There is a need for heating blanket covers that are easily manipulated for placing a heating blanket therein and do not compromise the comfort of a person over which the blanket is placed.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIGS. 1A-B are top and end views, respectively, of a heating blanket cover, according to some embodiments of the present invention.

FIGS. 2A-B are top and end views, respectively, of the blanket cover of FIGS. 1A-B closed over a heating blanket.

FIGS. 3A-C are section views illustrating a method for keeping a patient, upon a bed or an operating table, warm, by employing the cover of FIGS. 1A-2B.

FIGS. 4A-B are section views illustrating alternate methods for securing the cover about the patient.

FIGS. 5A-B are top and end views, respectively, of a heating blanket cover, according to some alternate embodiments of the present invention.

FIGS. 7-8 are top views of heating blanket covers, according to some alternate embodiments of the present invention.

FIGS. 9A-B are top views of a heating blanket cover, according to additional alternate embodiments of the present invention.

DETAILED DESCRIPTION

Figure 6A:
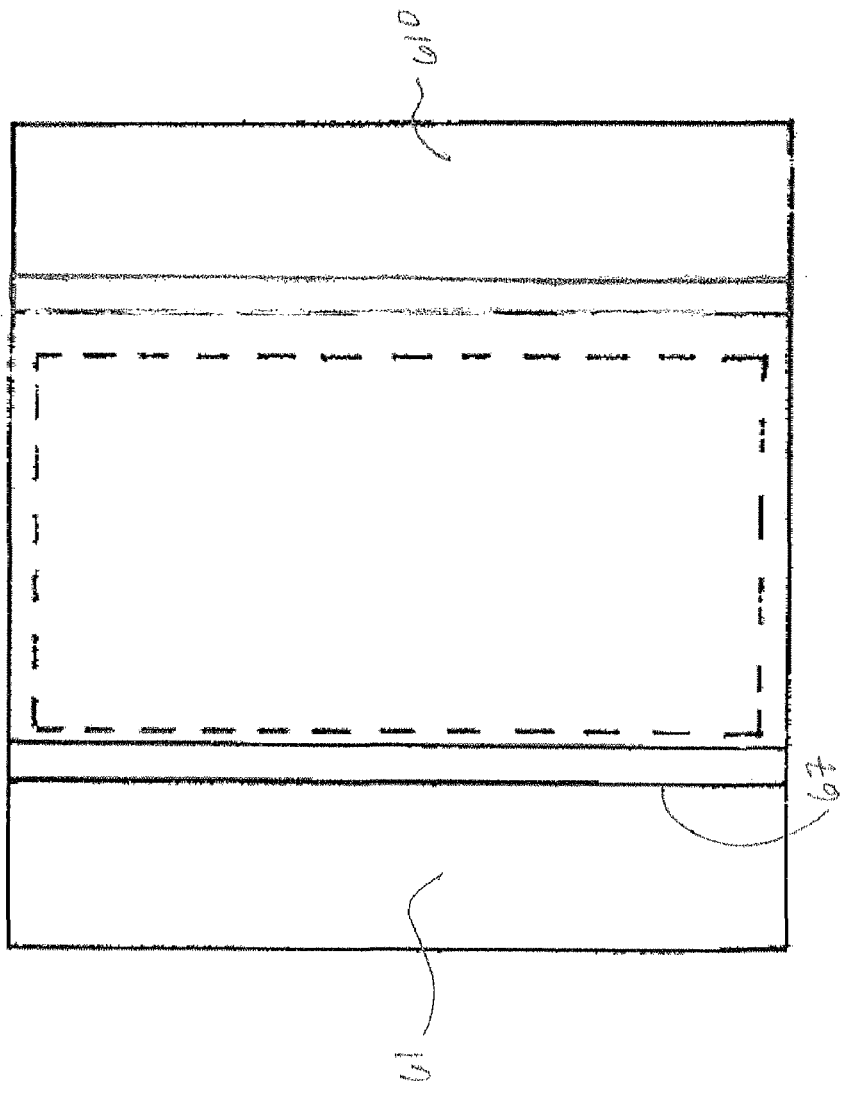
FIGS. 6A-B are top and end views, respectively, of the blanket cover of FIGS. 5A-B closed over a heating blanket.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

FIGS. 1A-B are a top view and an end view of a heating blanket cover 100 according to some embodiments of the present invention. FIGS. 1A-B illustrate cover 100 including a first or lower flexible sheet 10 to which a second or upper flexible sheet 14 is bonded, which upper flexible sheet 14 includes a first panel 15 and a second panel 150; bonding sites 16 and 160 of upper flexible sheet 14 may either extend continuously along a length L of panels 15, 150 or may be formed as a series of discrete sites disposed along length L. Although bonding sites 16, 160 are illustrated having a generally narrow width, in alternate embodiments the bonding sites may be wider if upper sheet 14 extends further laterally over lower sheet 10, according to the arrows in FIG. 1B. First and second panels 15, 150 extend from bonding sites 16, 160, respectively, to a first free edge 17 (panel 15) of upper sheet 14 and a second free edge 170 (panel 160) of upper sheet 14, and are illustrated folded back away from one another. It should be noted that, according to alternate embodiments, lower sheet 10 may extend beyond length L in one or both directions.

FIGS. 1A-B further illustrate a reusable heating blanket 1 disposed upon lower flexible sheet 10 between bonding sites 16, 160. According to the illustrated embodiment, the area on lower sheet upon which blanket 1 is disposed will form a boundary of an enclosure 2 (FIG. 2B) that is easily accessible by folding back panels 15, 150 of the upper sheet, as illustrated. FIGS. 2A-B are a top and end view of cover 100 wherein panels 15, 150 are closed over heating blanket 1. According to the illustrated embodiment, an overlap junction 19 of panels 15, 150 helps to secure heating blanket 1 within enclosure 2 although free ends 51, 52 of panel 15 and free ends 53, 54 of panel 150 may not be closed against bottom sheet 10. FIG. 2A further illustrates cover 100 having a length L' generally corresponding to a length of heating blanket 1; length L' may either be sufficient to cover a person from head to toe or may be shorter to just cover a portion of a person, leaving an area of the person exposed, for example a patient undergoing an operation and having a surgical site exposed.

According to some embodiments of the present invention, one or both of panels 15, 150 include one or more reversible fastening elements disposed in proximity to respective edges 17, 170. These elements could include fasteners that are disposed at discrete points along edges 17, 170, for example button type or snap-fit type fasteners; or fasteners that include discretely disposed elements along just one of the edges, i.e. edge 170, and a continuous strip element extending along mating edge 17, to which the discretely disposed elements may be reversibly fastened; or continuous strip fastening elements extending along both edges 17, 170. FIGS. 1A-B illustrate an embodiment wherein a strip of fastening material 18 extends along panel edge 17, and a mating fastening element 180, which may be a strip element or a series of discrete elements, is disposed along panel edge 170. Examples of reversible fastening elements 18, 180 include, but are not limited to: a strip of a loop material appropriate for hook-and-loop type fastening, which could be extruded into the upper sheet, for mating with a strip or patches of hook material; and a strip of polymer for mating with a strip or patches of tacky or adhesive material. According to alternate embodiments of the present invention, panels 15, 150, may be passively secured over blanket 1, without fastening elements, either by a weight of panels or by friction between panels at overlap junction 19.

According to some alternate embodiments of the present invention, blanket 1 is not completely enclosed by cover 100 in enclosure 2. For example, panel 15 may not overlap panel 150 and a gap may exist between free edges 17, 170 when panels 15, 150 are closed over blanket 1, and/or a length of blanket 1 may be longer than either or both of lengths L and L'.

FIGS. 2A-B further illustrate cover 100 including lateral portions or flaps 11 and 110 extending laterally beyond enclosure 2. According to certain embodiments of the present invention flaps 11, 110 are useful for holding heating blanket 1 in place over a patient, as will be described in conjunction with FIGS. 4 and 5.

FIGS. 3A-C are section views illustrating a method for keeping a patient 30, upon a bed or operating table 35, warm, by employing cover 100 and heating blanket 1. Cover 100 provides a clean interface between reusable heating blanket 1 and patient 30 so that the expense of having to clean heating blanket 1 between uses may be avoided. FIG. 3A shows cover 100 having been placed over patient 30 with upper flexible sheet panels 15, 150 being open to expose lower flexible sheet 10. Panels 15, 150 would, preferably, be opened after placing cover 100 over patient 30, but the scope of the present invention is not limited as such. FIG. 3B shows heating blanket 1 having been placed upon lower sheet 10 between bonding sites 16, 160; and FIG. 3C shows panels 15, 150 having been closed over blanket 1 to envelop blanket 1 between the upper and lower sheets, within enclosure 2, and panels 15, 150 having been secured over blanket 1 by fastening elements 18, 180 at junction 19. Although FIGS. 3A-C illustrate a preferred method where cover 100 is placed over patient 30 prior to placing heating blanket 1 in cover enclosure 2, an alternate method of placing blanket 1 in cover enclosure 2 before placing cover 100 over patient 30 is within the scope of the present invention. It may be appreciated from FIGS. 3A-C the ease with which blanket 1 is placed within cover 100.

According to certain embodiments of the present invention, lower flexible sheet 10 is flexible enough to drape over and conform with contours of patient 30, and sheet 10 includes a relatively soft lower surface to make a comfortable interface with patient 30. Accordingly, sheet 10 may be formed of a layer of fibrous material, woven or non-woven, examples of which include, but are not limited to, polyester, polypropylene, nylon, rayon and cellulose, i.e. from wood pulp fibers. According to some embodiments of the present invention, the layer of fibrous material is laminated with a layer of polymeric material, examples of which include, but are not limited to, polyethylene, polypropylene, polyolefin, ethylvinylacetate (EVA) and polyurethane. Alternate laminating means include, but are not limited to, adhesive bonding, heat bonding and extrusion coating. The polymeric material layer of a laminated lower flexible sheet 10 forms an upper surface on which heating blanket 1 would be laid, and to which the upper flexible sheet would be bonded. Methods for bonding the upper flexible sheet to lower flexible sheet 10 include, but are not limited to, adhesive, thermal and ultrasonic. The upper flexible sheet may be formed of a single layer of polymeric film, or may be a layer of fibrous material laminated with a polymeric material, similar to lower sheet 10. Preferably, a material or materials selected for the upper flexible sheet would provide some thermal insulation between heating blanket 1 and an area above cover 100, while a material or materials selected for lower flexible sheet 10 would allow efficient heat transfer between heating blanket 1 and patient 30. According to exemplary embodiments of the present invention, a lower sheet, for example, lower sheet 10, has a thickness ranging from approximately 0.5 oz/yd$^2$ (17 g/meter$^2$) to approximately 3 oz/yd$^2$ (100 g/meter$^2$), and is either comprised of spunbond polypropylene laminated with low density polyethylene, or spunbond/meltblown/spunbond polypropylene laminated with polyolefin; and an upper sheet, for example, upper sheet 14, has a thickness ranging from approximately 0.0005 inch (0.0125 mm) to approximately 0.004 inch (0.102 mm), and is either comprised of low density polyethylene (LDPE) or a blend of LDPE and EVA.

FIGS. 3A-C further illustrate flaps 11, 110 of cover 100 draping over sides of operating table 35 and extending laterally over a limited length so as not to extend to the ground or floor beside table 35; accordingly, flaps 11, 110 may extend laterally over a length between approximately 1 foot and approximately 4.5 feet. Referring back to FIG. 2A, flaps 11, 110, according to one embodiment of the present invention, include perforations 12 and 120 extending therethrough in a lateral direction so that tie strips 13 and 130 may be separated from a remainder of flaps 11, 110 in order to secure cover 100 about a patient, for example patient 30 on operating table 35 as illustrated in FIG. 4A. FIG. 4A shows tie strips 13, 130 tied to table legs 36, 360. Alternately strips 13, 130 could be tied together to secure cover 100 about a person. According to an alternate embodiment, perforations 12, 120 are not included and flaps 11, 110 are simply tucked around sides of a patient, for example patient 30, as illustrated in FIG. 4B.

FIGS. 5A-B are a top view and an end view of a cover 200 according to alternate embodiments of the present invention. FIG. 5A illustrates cover 200 including a lower flexible sheet 20 to which an upper flexible sheet 60 is bonded; a panel 65 of upper flexible sheet 60, shown folded away from lower flexible sheet 20, extends from a bonding site 66 to a free edge 67 of sheet 60. Bonding site 66 may extend along a length L" of panel 65 and, although bonding site 66 is illustrated having a relatively narrow width, site 66 may be wider if upper sheet 60 extends further laterally over lower sheet 20, according to the arrow in FIG. 5B. It should be noted that, according to some alternate embodiments, lower sheet 20 extends beyond length L" in one or both directions.

Figure 6B:
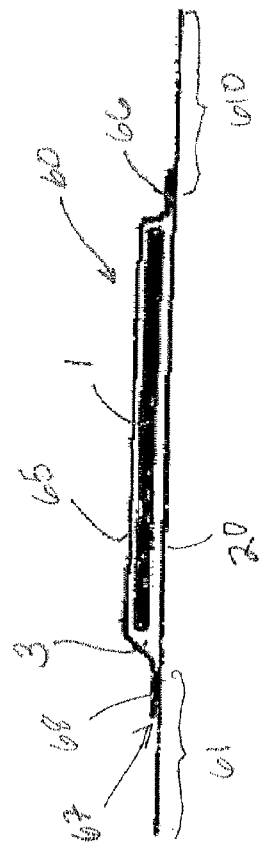

FIGS. 5A-B further illustrate heating blanket 1 disposed upon lower flexible sheet 20 adjacent bonding site 66 which forms an edge of an enclosure 3 when panel 65 is closed over blanket 1, as illustrated in FIGS. 6A-B. From FIGS. 5A-B and 6A-B, the ease with which blanket 1 may be placed in enclosure 3, by first folding back panel 65 and then closing panel 65 over blanket 1, may be appreciated. Panel 65 may be reversibly fastened to lower sheet 20 in order to secure blanket 1 within enclosure 3. FIGS. 5A-B illustrate a preferred embodiment in which a strip of fastening material 68, for example an adhesive strip, extends along length L" of panel 65 in proximity to free edge 67. FIGS. 6A-B illustrate strip 68 of panel 65 adhered to lower flexible sheet 20 to secure blanket 1 within enclosure 3. According to alternate embodiments, lower sheet 20 and panel 65 include mating fastening elements, examples of which include, but are not limited to, hook-and-loop type, button type and snap-fit type; alternative forms of fastening elements, previously described in conjunction with cover 100 illustrated in FIGS. 1A-2B, are appropriate alternatives for cover 200.

According to alternate embodiments of the present invention, blanket 1 is not completely enclosed by cover 200 in enclosure 3. For example, panel 65 may not extend completely over blanket as is illustrated in FIGS. 6A-B, and/or blanket 1 may be longer than length L".

FIGS. 6A-B further illustrate flaps 61 and 610 extending from either side of enclosure 3.

Similar to flaps 11, 110 of cover 100, flaps 61, 610 extend laterally over a sufficient length so that flaps 61, 610 may be tucked around sides of a patient on an operating table, i.e. patient 30 on table 35 (FIGS. 3A-B and 4B). A method for warming a patient using cover 200 would generally correspond to that described for cover 100, in conjunction with FIGS. 3A-B. Furthermore, cover 200 may include perforations through flaps 61, 610 to form tie strips, similar to tie strips 13, 130 of cover 100 illustrated in FIGS. 2A and 4A.

Similar to cover 100 previously described, lower flexible sheet 20 of cover 200, according to a preferred embodiment, is flexible enough to drape over and conform with contours of a patient, i.e. patient 30 (FIGS. 3A-C), and, furthermore, includes a relatively soft lower surface to make a comfortable interface with the patient. Thus, lower flexible sheet 20 may be formed of any of the materials previously described for lower flexible sheet 10 of cover 100; likewise sheet 20 may be laminated with a layer of polymeric material, for example any of those previously described, which forms an upper surface of sheet 20 on which blanket 1 is laid and to which upper flexible sheet 60 is bonded. Methods for bonding upper flexible sheet 60 to lower flexible sheet 20 include, but are not limited to, adhesive, thermal and ultrasonic. Upper flexible sheet 60 may be formed of a single layer of polymeric film, or may be a layer of fibrous material laminated with a polymeric material, similar to lower sheet 20. Preferably, a material or materials selected for upper flexible sheet 60 would provide some thermal insulation between heating blanket 1 and an area above cover 200, while a material or materials selected for lower flexible sheet 20 would allow efficient heat transfer between heating blanket 1 and patient disposed beneath cover 200.

FIG. 7 is a top view of a cover 300 according to another embodiment of the present invention. Similar to cover 100 described in conjunction with FIGS. 1A-4B, cover 300 is illustrated including a lower flexible sheet 80 to which an upper flexible sheet 85 is bonded, upper flexible sheet 85 including a first panel 89 and a second panel 890. Panels 89, 890 extend from respective bonding sites 86 and 860 to respective free edges 87 and 870 of upper flexible sheet 85, and are shown closed such that panel 89 overlaps panel 890 to envelop a heating blanket (not shown) between the upper flexible sheet and lower flexible sheet 80. It should be noted that ends 41, 42 of panel 89 and ends 43, 44 of panel 890 are not attached to lower sheet 80 allowing panels 89 and 890 to be folded open similar to panels 15 and 150 of cover 100 illustrated in FIG. 1B.

FIG. 7 further illustrates upper flexible sheet including a head portion 810 (corresponding to a head of a patient that would be disposed beneath cover 300) extending longitudinally from the enclosure and terminating at a head edge 81. According to some embodiments of the present invention, an underside of portion 810 includes an absorbent interface for absorbing airway secretions of the patient; according to some alternate embodiments portion 810 may be formed of a clear plastic film so that the patient disposed beneath cover 80 may be viewed through head portion 810 by a person above cover 80. According to alternate embodiments, head portion 810 is an extension of upper sheet 85.

FIG. 8 is a top view of a cover 400, according to yet another embodiment of the present invention. FIG. 8 illustrates cover 400 including a lower flexible sheet 90 to which an upper flexible sheet 95 is bonded at bonding site 96, which extends longitudinally and laterally. According to the illustrated embodiment, upper flexible sheet 95 includes a panel 99 extending laterally from the longitudinally extending portion of bonding site 96 to a free edge 97 of upper sheet 95; a second free edge 92 of panel 99 extends alongside the lateral extension of bonding site 96 and may have been formed by cutting upper sheet 95. It should be noted that end 45 of panel is not attached to lower sheet 90 so that panel 99 may be folded back similar to panel 65 of cover 200 illustrated in FIG. 6B. FIG. 8 further illustrates panel 99 closed over lower flexible sheet 90, to envelop a heating blanket between lower flexible sheet 90 and upper flexible sheet 95, and upper flexible sheet 95 further including a head portion 910 extending longitudinally from bonding site 96, beyond lower flexible sheet 90, to a head edge 91. Head portion 910 is shown transparent but may additionally or alternately include an underside having absorbent properties. According to alternate embodiments, head portion 910 is an extension of lower sheet 90.

FIGS. 9A-B are top views of a heating blanket cover 500, according to additional alternate embodiments of the present invention. FIG. 9A illustrates cover 500 including a lower flexible sheet 70 to which an upper flexible sheet 75 is bonded; a panel 79 of upper sheet 75, shown opened away from lower sheet 70, extends from a bonding site 76 to a free edge 77 of upper sheet 75. FIG. 9A further illustrates a heating blanket 101 disposed on lower flexible sheet 70 for enclosure between upper sheet 75 and lower sheet 70 when panel 79 is folded over, as illustrated in FIG. 9B. Blanket 101, being shaped for an upper body portion of a person whose arms are outstretched, includes a central region 72, to cover a chest of the person, and two end regions 71, to cover the outstretched arms. FIG. 9B illustrates a head portion 78 of folded-over panel 79 extending beyond an opposite edge of lower sheet 70; head portion 76 may enclose a head of the person beneath cover 500 and blanket 101 to prevent heat loss therefrom. According to the illustrated embodiment, panel 79 is transparent so that the head of the person beneath cover 500 can be seen from the opposite side of cover 500. According to the illustrated embodiment, a length L5 of lower sheet 70 of cover 500 is long enough to accommodate an entire length of blanket 101, however, according to alternate embodiments, length L5 need not accommodate an entire length of blanket 101 extending only approximately between end regions 71. Additionally, although a length of upper sheet 75 is shown being less than L5, the length of upper sheet 75 may be equal to L5.

Each of the alternate embodiments described in conjunction with FIGS. 7, 8 and 9A-B may include any of the features previously described for other cover embodiments and may be formed of similar materials and according to similar construction methods.

In the foregoing detailed description, the invention has been described with reference to specific embodiments. However, it may be appreciated that various modifications and changes can be made without departing from the scope of the invention as set forth in the appended claims. Furthermore, although embodiments of the invention are described in the context of a hospital, particularly in an operating room, it is contemplated that the invention may be used in other environments.

The invention claimed is:

1. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge;
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure; and
   a fastening element coupled to the at least one panel to reversibly secure the heating unit within the enclosure beneath the panel;
   wherein the bonding site of the upper to lower sheet includes a first bonding site and a second bonding site opposite the first bonding site;
   the at least one panel of the upper sheet includes a first panel and a second panel;
   the free edge of the upper sheet includes a first free edge and second free edge;
   the first panel extends toward the second panel, from the first bonding site to the first free edge;
   the second panel extends toward the first panel, from the second bonding site to the second free edge and overlaps a portion of the first panel; and
   the fastening element is disposed at the overlap of the panels.

2. The cover of claim 1, wherein the lower sheet has characteristics to provide efficient heat transfer therethrough from the heating blanket held in the enclosure.

3. The cover of claim 1, wherein the lower sheet includes an outer surface having characteristic to provide a relatively soft interface with a patient disposed beneath the cover.

4. The cover of claim 1, wherein the upper sheet has characteristics to provide insulation between the heating blanket held in the enclosure and an area outside the enclosure on an opposite side of the upper sheet.

5. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge; and
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure; and
   wherein the bonding site of the upper sheet to the lower sheet includes a first bonding site and a second bonding site opposite the first bonding site;
   the at least one panel of the upper sheet includes a first panel and a second panel;
   the free edge of the upper sheet includes a first free edge and second free edge;
   the first panel extends toward the second panel, from the first bonding site to the first free edge; and
   the second panel extends toward the first panel, from the second bonding site to the second free edge.

6. The cover of claim 5, wherein the lower sheet includes an outer surface having characteristic to provide a relatively soft interface with a patient disposed beneath the cover.

7. The cover of claim 5, wherein the upper sheet has characteristics to provide insulation between the heating blanket held in the enclosure and an area outside the enclosure on an opposite side of the upper sheet.

8. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge; and
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure; and
   wherein at least one of the upper and lower sheets extends laterally beyond the enclosure over a length greater than approximately one foot.

9. The cover of claim 5, wherein the lower sheet has characteristics to provide efficient heat transfer therethrough from the heating blanket held in the enclosure.

10. The cover of claim 8, wherein the lower sheet has characteristics to provide efficient heat transfer therethrough from the heating blanket held in the enclosure.

11. The cover of claim 8, wherein the lower sheet includes an outer surface having characteristic to provide a relatively soft interface with a patient disposed beneath the cover.

12. The cover of claim 8, wherein the upper sheet has characteristics to provide insulation between the heating blanket held in the enclosure and an area outside the enclosure on an opposite side of the upper sheet.

13. The cover of claim 8, wherein the bond is linear to produce a linear bonding site.

14. The cover of claim 8, further comprising a fastening element coupled to the at least one panel to reversibly secure the heating unit within the enclosure beneath the panel.

15. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge;
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure;
   a first flap extending laterally beyond the enclosure from the first edge of the enclosure; and
   a second flap extending laterally beyond the enclosure from a second edge of the enclosure, the second edge of the enclosure being opposite the first edge;
   wherein the first and second flaps are extensions of at least one of the upper and lower sheets.

16. The cover of claim 15, wherein each of the first and second flaps extends over a length greater than approximately one foot.

17. The cover of claim 15, wherein each of the first and second flaps extends over a length sufficient to allow the flaps to be wrapped about opposite sides of an average person disposed beneath the cover.

18. The cover of claim 15, wherein each of the first and second flaps includes at least one tie strip for securing the cover about a person.

19. The cover of claim 15, wherein each of the first and second flaps includes perforations extending therethrough to form at least one tie strip for securing the cover about a person.

20. The cover of claim 15, wherein the bond is linear to produce a linear bonding site.

21. The cover of claim 15, further comprising a fastening element coupled to the at least one panel to reversibly secure the heating unit within the enclosure beneath the panel.

22. The cover of claim 15, wherein the lower sheet has characteristics to provide efficient heat transfer therethrough from the heating blanket held in the enclosure.

23. The cover of claim 15, wherein the lower sheet includes an outer surface having characteristic to provide a relatively soft interface with a patient disposed beneath the cover.

24. The cover of claim 15, wherein the upper sheet has characteristics to provide insulation between the heating blanket held in the enclosure and an area outside the enclosure on an opposite side of the upper sheet.

25. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge;
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure; and
   a head portion extending longitudinally beyond the enclosure, the head portion being an extension of at least one of the upper and lower sheets.

26. The cover of claim 25, wherein the head portion includes an absorbent lower surface to interface with a person disposed beneath the cover.

27. The cover of claim 25, wherein the head portion includes a transparent portion for visualizing a person disposed beneath the cover through the cover.

28. The cover of claim 25, wherein the head portion is an extension of the upper sheet beyond the lower sheet.

29. The cover of claim 25, wherein the bond is linear to produce a linear bonding site.

30. The cover of claim 25, further comprising a fastening element coupled to the at least one panel to reversibly secure the heating unit within the enclosure beneath the panel.

31. The cover of claim 25, wherein the lower sheet has characteristics to provide efficient heat transfer therethrough from the heating blanket held in the enclosure.

32. The cover of claim 25, wherein the lower sheet includes an outer surface having characteristic to provide a relatively soft interface with a patient disposed beneath the cover.

33. The cover of claim 25, wherein the upper sheet has characteristics to provide insulation between the heating blanket held in the enclosure and an area outside the enclosure on an opposite side of the upper sheet.

34. A cover for protecting a heating blanket, the cover comprising:
   a lower flexible sheet;
   an upper flexible sheet bonded to the lower flexible sheet at a bonding site, the upper sheet including at least one panel and a free edge, the at least one panel extending from the bonding site to the free edge; and
   a bond between the upper and lower sheets at a bonding site, the bond creating one edge of an enclosure for holding the heating blanket between the upper and lower sheets, the at least one panel being separable from the lower sheet, by lifting the free edge of the upper sheet, in order to fold back the panel, along the bonding site, and to, thereby, provide an opening for accessing the enclosure; and
   wherein at least one of the upper and lower sheets includes a first layer and a second layer, the first layer forming an outer surface of the covering and the second layer forming an inner surface of the enclosure.

35. The cover of claim 34, wherein the first layer is formed from a cellulose material and the second layer is formed of a polymeric material.

36. The cover of claim 34, wherein the first and second layers are formed of polymeric materials.

37. The cover of claim 34, wherein the first layer is laminated to the second layer.

38. The cover of claim 34, wherein the bond is linear to produce a linear bonding site.

39. The cover of claim 34, further comprising a fastening element coupled to the at least one panel to reversibly secure the heating unit within the enclosure beneath the panel.

40. The cover of claim 34, wherein the lower sheet has characteristics to provide efficient heat transfer therethrough from the heating blanket held in the enclosure.

41. The cover of claim 34, wherein the upper sheet has characteristics to provide insulation between the heating blanket held in the enclosure and an area outside the enclosure on an opposite side of the upper sheet.

42. A method of claim 23, further for warming a patient, the method comprising:
- placing a cover over the patient;
- opening an enclosure formed between an upper sheet and a lower sheet of the cover, to expose an underlying surface of the lower sheet, by folding back a panel of the upper sheet along a bonding site, at which a bond is formed between the upper sheet and the lower sheet;
- placing a heating blanket upon the underlying portion of the lower sheet, within the enclosure;
- closing the panel over the heating blanket; and
- wrapping a flap of the cover about a side of the patient, the flap extending laterally beyond the enclosure.

43. The method of claim 42, further comprising reversibly fastening the panel in place over the heating blanket that is placed in the enclosure.

44. The method of claim 42, wherein placing the cover follows placing the heating blanket.

45. A method for warming a patient, the method comprising:
- placing a cover over the patient;
- opening an enclosure formed between an upper sheet and a lower sheet of the cover, to expose an underlying surface of the lower sheet, by folding back a panel of the upper sheet along a bonding site, at which a bond is formed between the upper sheet and the lower sheet;
- placing a heating blanket upon the underlying portion of the lower sheet, within the enclosure;
- closing the panel over the heating blanket; and
- securing the cover about the patient by tying together tie strips of the cover, the strips extending laterally beyond the enclosure from opposite edges of the enclosure.

46. The method of claim 45, further comprising reversibly fastening the panel in place over the heating blanket that is placed in the enclosure.

47. The method of claim 45, wherein placing the cover follows placing the heating blanket.

48. A method for warming a patient, the method comprising:
- placing a cover over the patient;
- opening an enclosure formed between an upper sheet and a lower sheet of the cover, to expose an underlying surface of the lower sheet, by folding back a panel of the upper sheet along a bonding site, at which a bond is formed between the upper sheet and the lower sheet;
- placing a heating blanket upon the underlying portion of the lower sheet, within the enclosure;
- closing the panel over the heating blanket; and
- securing the cover about the patient, by tying strips of the cover to sides of a bed on which the patient is lying, the strips extending laterally beyond the enclosure from opposite edges of the enclosure.

49. The method of claim 48, further comprising reversibly fastening the panel in place over the heating blanket that is placed in the enclosure.

50. The method of claim 48, wherein placing the cover follows placing the heating blanket.

\* \* \* \* \*